United States Patent
Yao et al.

(10) Patent No.: US 10,542,736 B2
(45) Date of Patent: Jan. 28, 2020

(54) LARGE-SCALE AND HIGH-EFFICIENCY FLY MAGGOT CULTURING EQUIPMENT AND PROCESS

(71) Applicant: ZHEJIANG ACADEMY OF AGRICULTURAL SCIENCES, Hangzhou (CN)

(72) Inventors: Yanlai Yao, Hangzhou (CN);
Fengxiang Zhu, Hangzhou (CN);
Weiping Wang, Hangzhou (CN);
Chunlai Hong, Hangzhou (CN);
Xiaoyang Chen, Hangzhou (CN);
Hongquan Yang, Hangzhou (CN);
Zhiyong Xue, Hangzhou (CN)

(73) Assignee: ZHEJIANG ACADEMY OF AGRICULTURAL SCIENCES, Hangzhou (CN)

( * ) Notice: Subject to any disclaimer, the term of this patent is extended or adjusted under 35 U.S.C. 154(b) by 285 days.

(21) Appl. No.: 15/327,787

(22) PCT Filed: Jul. 29, 2015

(86) PCT No.: PCT/CN2015/085391
§ 371 (c)(1),
(2) Date: Jan. 20, 2017

(87) PCT Pub. No.: WO2016/015639
PCT Pub. Date: Feb. 4, 2016

(65) Prior Publication Data
US 2018/0206463 A1    Jul. 26, 2018

(30) Foreign Application Priority Data

Jul. 31, 2014 (CN) .......................... 2014 1 0372379
Aug. 14, 2014 (CN) .......................... 2014 1 0399299
Nov. 26, 2014 (CN) .......................... 2014 1 0686525

(51) Int. Cl.
*A01K 67/033* (2006.01)
*C05F 17/00* (2006.01)

(52) U.S. Cl.
CPC ........ *A01K 67/033* (2013.01); *C05F 17/0009* (2013.01)

(58) Field of Classification Search
CPC .............................. A01K 67/033; A01K 67/00
See application file for complete search history.

(56) References Cited

U.S. PATENT DOCUMENTS 6,561,125 B1 * 5/2003 Lohsomboon ....... A01K 67/033
119/416
2009/0295774 A1 * 12/2009 Okamoto ............... G11C 5/063
345/211

(Continued)

FOREIGN PATENT DOCUMENTS

WO    WO-2013151207 A1 * 10/2013 ........... A01K 67/033

*Primary Examiner* — Monica L Williams
(74) *Attorney, Agent, or Firm* — IPro, PLLC (57) ABSTRACT

The present invention provides a set of large-scale and high-efficiency fly maggot culture equipment and a large-scale and high-efficiency fly maggot culture process and pertains to fly maggot culture. The equipment comprises at least one culturing workshop with a multi-functional ceiling. At least one feeder traveling along double-row burden distributing rails is arranged in the culturing workshop. A pair of main rails is perpendicularly arranged on the front of one ends of the burden distributing rails. A rail car used for transferring the feeder among different burden distributing rails is arranged on the main rails. Transferring rails horizontally perpendicular to the main rails are arranged on the rails car. The height of the transferring rails is consistent with the height of the distributing rails. The workshop ground between the two rails of the distributing rails form a culturing bed for fly maggot culture. The equipment also includes a central control apparatus connected with an alarm (Continued)

and a fly maggot separator. The equipment and the process provided in this present invention can realize incessant fly maggot flow line culture, without being affected by temperature, and is much highly automatic to realize fly maggot production in large scale and with high effectiveness.

12 Claims, 8 Drawing Sheets

(56) References Cited

U.S. PATENT DOCUMENTS

| | | | |
|---|---|---|---|
| 2012/0189549 A1* | 7/2012 | Claridge-Chang | A01K 29/005 424/9.2 |
| 2014/0261188 A1* | 9/2014 | Chin | A01K 67/033 119/6.6 |
| 2015/0296760 A1* | 10/2015 | Perednia | A01K 67/033 119/6.5 |
| 2015/0359208 A1* | 12/2015 | Reckhaus | G01N 33/5085 119/6.5 |
| 2017/0202191 A1* | 7/2017 | Marchant | A01K 67/033 |

* cited by examiner

LARGE-SCALE AND HIGH-EFFICIENCY FLY MAGGOT CULTURING EQUIPMENT AND PROCESS

FIELD OF THE INVENTION

The present invention relates to fly maggot culture, and more particularly, to a set of large-scale and high-efficiency fly maggot culture equipment and a large-scale and high-efficiency fly maggot culture process.

BACKGROUND ART

The prior art of the culture of fly maggot is mainly by means of box-type culturing, cage-type culturing and frame culturing, for example, the high-scale fly maggot culture equipment and process in application No. 201210116603 is the typical culturing method of these kind. Complicated in culturing method and process, a plurality of steps in the prior art requires man participation, with intense labor but low efficiency. The prior art fits only for small-scale production and cannot truly realize industrialized large-scale and high-efficiency production, severely constraining the industrialization and application of fly maggot culture.

When biomass waste is utilized in large-scale fly maggot culture, it requires feeding everyday. The prior art is realized by artificial feeding, costing much time and labor while without high-efficiency and good work environment for workers. With the development of society and the raising of labor cost, special types of work like biomass waste feeding suffer obviously. Hence, fly maggot culturing industry is in urgent need of an automatic feeder to lower enormously the labor intensity and promote feeding efficiency.

After the production of fly maggot with biomass waste, the prior art realizes the separation of fly maggot from the compost by manual operation of simple machines, costing much time and labor while without high-efficiency and good work environment for workers. While with the development of society and the raising of labor cost, special types of work like biomass waste feeding suffer obviously. Hence, fly maggot culturing industry is in urgent need of an automatic fly maggot separator to lower enormously the labor intensity and promote efficiency in the separation of fly maggot from the residue.

SUMMARY OF THE INVENTION

It is therefore an object of the present invention to overcome the disadvantages of the prior art fly maggot culturing with simple machines and to provide a large-scale and high-efficiency fly maggot culture equipment and a large-scale and high-efficiency fly maggot culture process, which does not have complicated culturing methods and processes, a plurality of steps requiring man participation, without intense labor and low efficiency. The present invention is fit for large-scale production and truly realizes industrialized large-scale and high-efficiency production, without constraining the industrialization and application of fly maggot culture.

The present invention adopts the technical scheme that constructs a large-scale and high-efficiency fly maggot culture equipment, wherein the equipment comprises at least one culturing workshop with a multi-functional ceiling. At least one feeder traveling along double-row burden distributing rails is arranged in the culturing workshop. A pair of main rails is perpendicularly arranged on the front of one ends of the burden distributing rails. A rail car used for transferring the feeder among different burden distributing rails is arranged on the main rails. Transferring rails horizontally perpendicular to the main rails are arranged on the rails car. The height of the transferring rails is consistent with the height of the burden distributing rails and the workshop ground between the two rails of the burden distributing rails form a culturing bed for fly maggot culture. The equipment further comprises central control apparatuses for controlling the work of the feeders and the rail cars, and central control apparatus is connected with an alarm. The equipment also includes at least one hopper, connected with or isolated from the culturing workshop. The equipment further comprises at least one material mixer, one fly maggot separator, one washing machine and one warm air dryer.

Further, the culturing bed is equipped with a temperature-controlled insulating layer, in turn comprising a contact layer and a thermally conductive layer. Heat-conducting medium containing water or oil is injected into thermally conductive layer. The thermally conductive layer is also surrounded with an electromagnetic heating tube. The electromagnetic heating tube is connected with a temperature controlling device in the culturing bed through electric circuit. The temperature controlling device has electric connection with the central control apparatus. Culturing bed temperature sensors uniformly arranged in the contact layer and medium temperature sensors in the heat-conducting medium also have electric connection with the temperature controlling device.

Further, the multi-functional ceiling comprises movable awnings controlled by air temperature control devices. The air temperature control devices have electric connection with the central control apparatus. Several transparent plastic ceilings are set under the movable awnings. Spouting water cooling pipes are installed between the plastic ceilings and the movable awnings and water collecting troughs for collecting water from rain water and stream from spouting water pipes are arranged between any two of the transparent plastic ceilings. The bottoms of the water collecting troughs are connected with water curtain inlet pipes under the plastic ceilings. Water curtain machines installed on walls at four sides of the multi-functional ceilings are connected with the water curtain inlet pipes. Water pumps are fixed to the water curtain inlet pipes. The water pumps and the water curtain machines all have electric connection with the air temperature control devices through electric circuit and the air temperature control devices with the central control apparatus.

The top and bottom of the plastic ceilings are all equipped with air temperature sensors and humidity sensors. A plurality of motorized roller shades are set on walls at four sides of the plastic ceilings and all the air temperature sensors, humidity sensors and motorized roller shades have electric connection with the air temperature control devices.

A data input device and a data output device are connected to the central control apparatus, and the data output device comprises a printer and a computer.

Further, the feeder includes a feeder cart traveling along the burden distributing rail. A movable platform on the feeder cart can move perpendicularly to the moving direction of the feeder cart, and a feeder control apparatus is mounted on the feeder cart. Mounting holes are prepared on the movable platform. A dismountable hopper is fixed in the mounting holes. At least one sub-hopper is connected to the bottom of the dismountable hopper. Dismountable injection nozzles are connected to the sub-hoppers. A feeding mechanism is arranged in the same axle of the dismountable injection nozzles. Two horizontal sliding rails are set at the both ends of the bottom of the movable platform and connect to the feeder cart. A ball screw is parallel with and arranged inside the slide at one side of the movable platform. The ball screw is connected to and driven by a second motor. A feeder control apparatus has electric connection with a second motor through electric circuit. And a first motor used to drive the rail car is arranged under the bottom of the feeder cart (3-2). The said first motor has electric connection with the feeder control apparatus. A first motor further includes continuously variable transmission.

The feeder cart is equipped with a manual signal input device and a wireless signal device, having electric connection with the feeder control apparatus. The manual signal input device comprises a digital liquid crystal display fixed on the feeder cart. The wireless signal device includes a handheld wireless signal transmitter and a wireless signal receiver fixed on the feeder cart and having electric connection with the feeder control apparatus.

Further, the feeding mechanism comprises at least one screw conveyor, with one end plugged into the injection nozzle and the other connected with the main axle of a third motor. A third motor is mounted on the feeder cart and a second motor has electric connection with the feeder control apparatus.

Further, the injection nozzle comprises a first nozzle, a second nozzle or a third nozzle. An open-close gate is given on a first nozzle, and a push rod is connected to the open-close gate. The push rod is welded to a stepping motor fixed on the feeder cart and the stepping motor has electric connection with the feeder control apparatus. The third nozzle includes a horizontally-laid "T" shaped hollow cylinder, comprising a connecting cylinder and a discharging cylinder. A horizontal screw conveyor is plugged in the connecting cylinder. At least three discharging outlets are set on the discharging cylinder and taintor valves are provided to the discharging outlets. A second nozzle comprises connectors connected with comigated flexible hoses capable of rotating 360 degrees.

Further, the fly maggot separator comprises a vehicle body and a feeding apparatus at the front of it. The feeding apparatus is connected to the front end of a groove-type hopper transporting fly maggots and compost residue and mounted on the vehicle body. A vertical hoisting device is provided to the hopper and equipped at the top with a cleaning apparatus capable of reciprocating motion perpendicular to the motion of the vehicle body. Two gates are suspended and connected with interconnecting linkages at both ends of the hoisting device. The gates are closely against the end faces of notches at two sides of the hopper and a collecting unit mounted on the vehicle is arranged under each of the end faces.

The feeding apparatus comprises a first conveyor belt driven by the motor of a first fly maggot separator. A reversible first material shovel is mounted at the front end of a first conveyor belt and push rods are set under a first material shovel.

The hoisting device comprises support frames suspending above the hopper. A first worm perpendicularly set in the side of the hopper and slide guiding rods are connected with the bottom of the supports. The vertically arranged spindle of the motor of a second fly maggot separator is connected to a first worm through gear cluster.

The cleaning apparatus comprises crossbar. A cleaning board is mounted at middle of the crossbar and perpendicularly suspended, and a slide block is fixed at one end of the crossbar. The slide block is overlapped on a slide rail at the top of the support. A second worm is arranged on the other end of the crossbar. The spindle of the motor of a third fly maggot separator horizontally set at the top of the support is connected with a second worm.

The collecting unit comprises a bevel residue collecting box and a bevel fly maggot collecting box. A first cover plate is arranged between the bevel residue collecting box and fly maggot collecting box and capable of pivoting and tightly closed both sides. Torsional springs are set at the pivoted end of a first cover plate. Electromagnetic switch locking portions are set at the other end of a first cover plate. The electromagnetic switch locking portions are matched respectively with electromagnetic locks on the bevel residue collecting box and the vehicle body and a limit switch for inducing the height of the gates is connected to the electromagnetic locks.

The vehicle body is equipped with suspending light source devices at the top of the cleaning apparatus. The both ends of the bottoms of the light source devices are all connected to the slide guiding rods and the light supplier is infrared light source or incandescent lamp.

A forth fly maggot separator motor for driving fly maggot separator is further installed under the vehicle body.

The vehicle body is further equipped with the control apparatus and the signal input device of the fly maggot separator. The control apparatus of the fly maggot separator is respectively and electrically connected with a first fly maggot separator motor, a second fly maggot separator motor, a third fly maggot separator motor, a forth fly maggot separator motor and signal input device and the signal input device comprises the touch screen of the fly maggot separator motor.

Further, the feeding apparatus comprises a second conveyor belt tilting down with at angle of no more than degree against the ground. A pivoting second material shovel is positioned at the front end of a second conveyor belt.

Further, the hopper is equipped with open-close bottom plates at the bottom. A fifth fly maggot separator motor is connected to the bottom plates through worms and gears and a fifth fly maggot separator motors have electric connection with the control apparatus of fly maggot separator.

The present invention provides a culture equipment process with the utilization of the culture equipment, comprising the following steps:

1, Material preparation, preparing the biomass waste in the hopper and adding the auxiliary materials therein, then adjusting the water ratio of the biomass waste with the material mixer, which serves as the compost or culturing base.

2, preparing and incubating fly-blows;

3, adjustment and preparation of the culture equipment. Adjusting and controlling the temperature of contact layer of the culturing bed between 25-37° C. and adjusting the environment temperature below 37° C.

4, at a first feeding of Day 1, utilizing the feeder to evenly and smoothly put a layer of culture medium in the culture bed as adjusted in step 1, ensuring the thickness of the culture medium within 1-5 centimeter and the water ratio 45%-75%, then scattering maggots as cultured in Step 2 into the culture medium, making sure that each gram of compost contains 2200-7000 maggots.

5, at a second feeding of Day 1, further adding the compost with a water ratio of 45%-95% and a volume of 1-20 kg/m2; and the time interval shall be 4 to 16 hours;

6, on Day 2, continuing to add culture medium of 45%-95% water ratio and repeating step 3 and step 5, ensuring that the amount of culture medium within 1-20 kg/m$^2$, the interval and steps of feeding the same as requested in step 3 and step 5, and ventilation at 1-2 times a day.

7, on Day 3 to Day n, continuing to add culture medium of 45%-95% water ratio and keeping the interval, steps, times and amount of culture medium adding and the ventilation frequency all the same as requested in step 5.

8, on Day n+1, stopping adding the compost, and then dividing the maggots in several culturing beds from the compost artificially or by using fly maggot separator;

9, washing the fly maggots as separated in the step 8 in the washing machine and conveying them to the warm air dryer to obtain the dried maggots. Preferably, the above-mentioned fly maggots are larvae of the housefly, Musca sorbens, Lucilia cuprina, Cluysomya megacephala, Phaenicia cuprina, Calliphora erythrocephala, Muscina stabulans, sarcophaga peregrina or soldier fly.

Preferably, the biomass waste utilized in the Step 1 is the animal waste, kitchen leftover or biomass processing waste. And the auxiliary materials are one or some combination of chicken or duck dung, extruded animal excrement, sawdust, rice chaff, spent mushroom compost, straw, tea residue and bran.

Compared with the prior art, an intermittent and assembly line-style culture equipment process of high degree of automation can be realized by way of the large-scale and high-efficiency fly maggot culture equipment and process disclosed by the present invention, free from the influence of weather and temperature, thus realizing large-scale and high-efficiency fly maggots production.

DESCRIPTION OF EMBODIMENTS

The present invention will be better understood by way of various specific details set forth in the following description. But the present invention may be embodied in various other ways different from the embodiments described herein, and those skilled in the art can make similar extensions without the breach of the content of the present invention. Accordingly, the embodiments of the present invention are not limited by the following disclosed specific embodiments.

Detailed description of various embodiments of the present invention will now be further illustrated by reference to the accompanying drawings and embodiments.

Embodiment 1

The structure of the present invention will be described in detail by reference to the accompanying drawings in this embodiment.

Please refer to FIG. 1 to FIG. 5. The large-scale and high-efficiency fly maggot culture equipment provided by the present invention comprises at least one culturing workshop of which each with a multifunction ceiling, wherein at least one feeder 3 traveling along double-row distributing rails 2 is disposed. In front of and perpendicular to one end of the distributing rails 2 a pair of main rails 4 are mounted, on which a rail 5 is arranged for transferring the feeder to different distributing rails. On the rail car 5 the transferring rails 6 are arranged horizontally perpendicular to the main rails 4 and the height is consistent with that of the distributing rails 2. The workshop ground between the two rails of the distributing rails 2 constitutes a culturing bed 7 for culture equipment. The equipment also comprises a central control device 8 connected with an alarm for controlling the operation of feeder 3 and track car 5. The equipment still comprises at least one hopper, which may be connected to the culturing workshop or arranged outside the workshop, and also comprises at least a material mixer, a fly maggot separator, a washing machine and a drier. With these auxiliary equipment of the whole large-scale and high-efficiency fly maggot culture equipment, a complete culture equipment process is formed, which is of high automation, high production efficiency and easier access to large-scale production.

Figure 1:
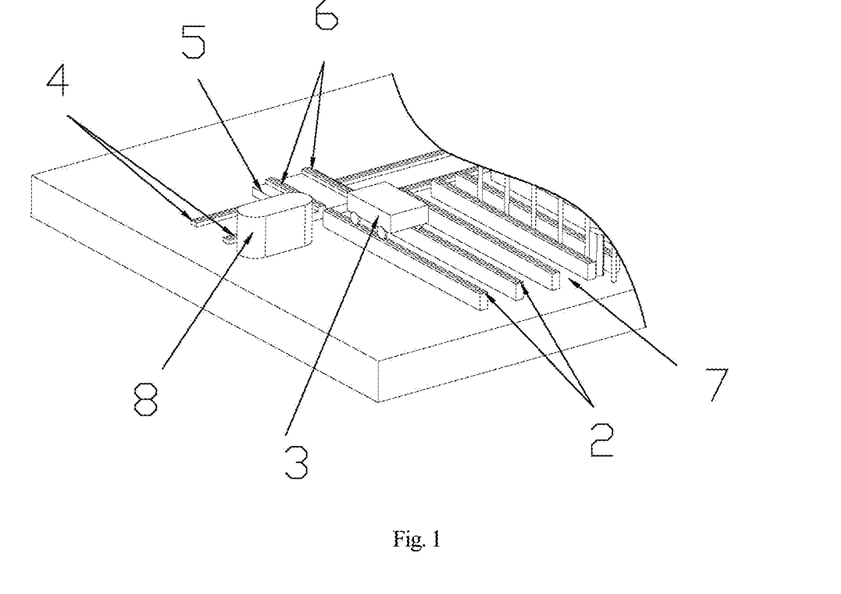
FIG. 1 is a structure diagram of culturing workshop of the present invention.
Figure 5:
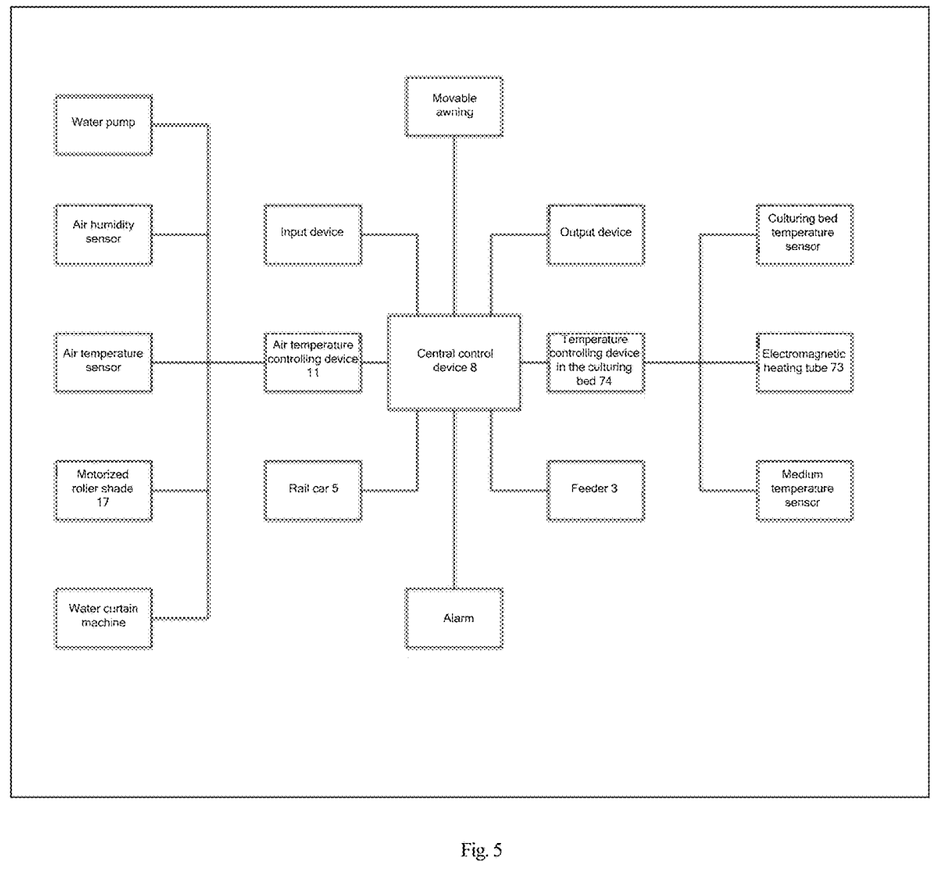
FIG. 5 is a schematic view of control principle of the present invention.
Figure 6:
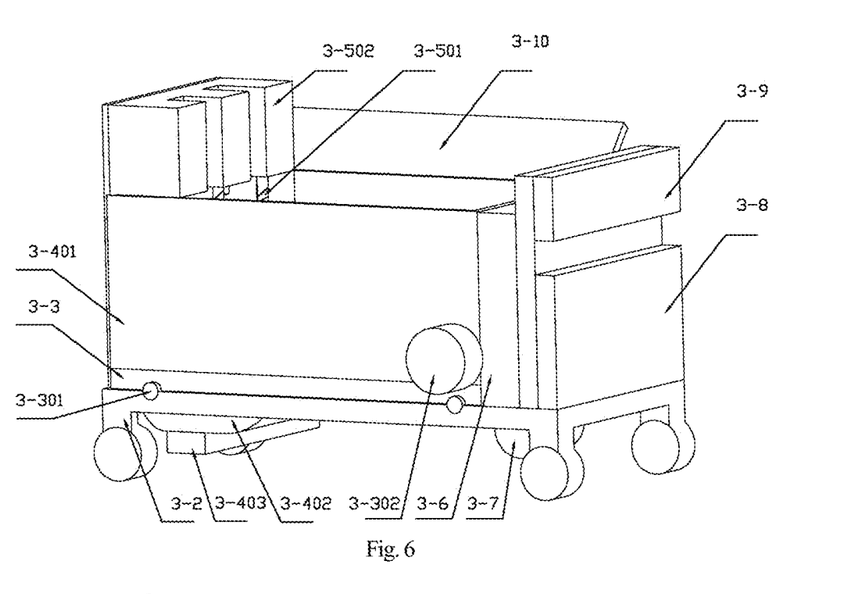
FIG. 6 is a schematic view of the feeder of the present invention.
Figure 7:
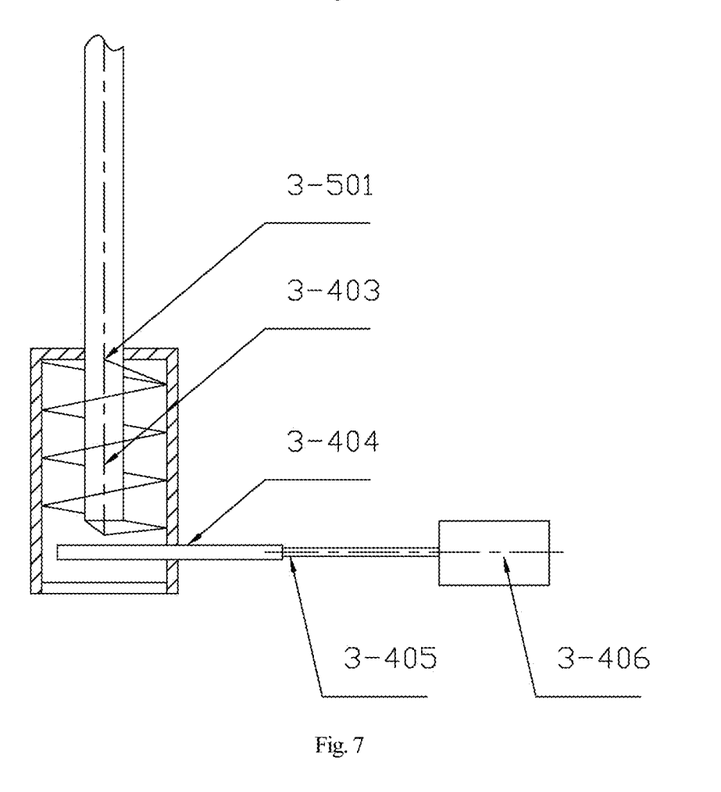
FIG. 7 is a schematic view of a first feed nozzle and feeding mechanism of the feeder of the present invention.
Figure 8:
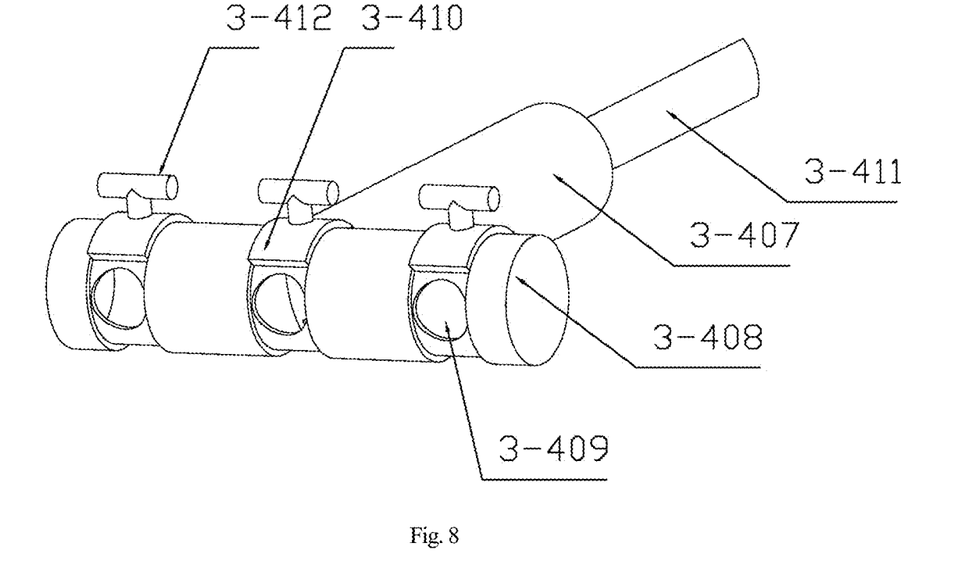
FIG. 8 is a schematic view of a second feed nozzle and feeding mechanism of the feeder of the present invention.
Figure 9:
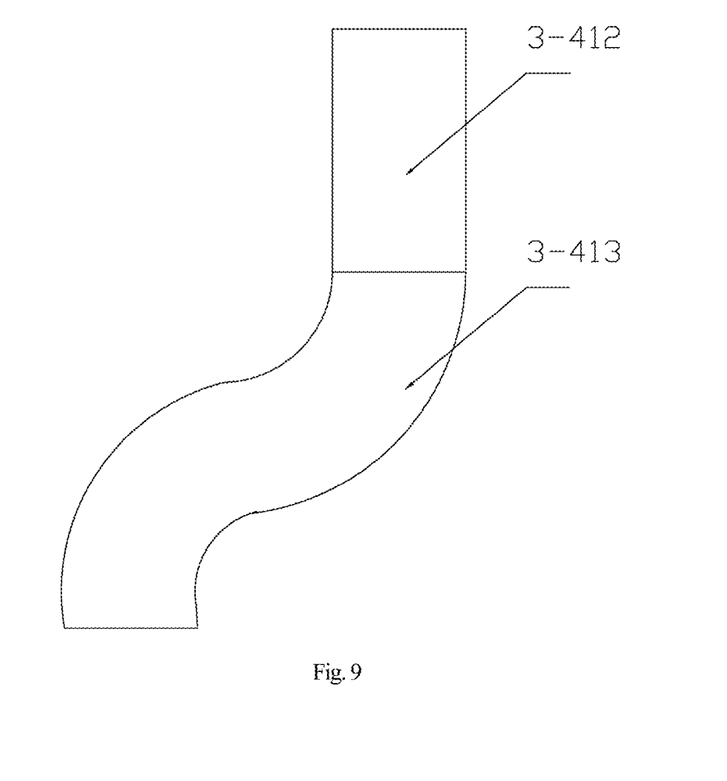
FIG. 9 is a schematic view of a third feed nozzle and feeding mechanism of the feeder of the present invention.
Figure 10:
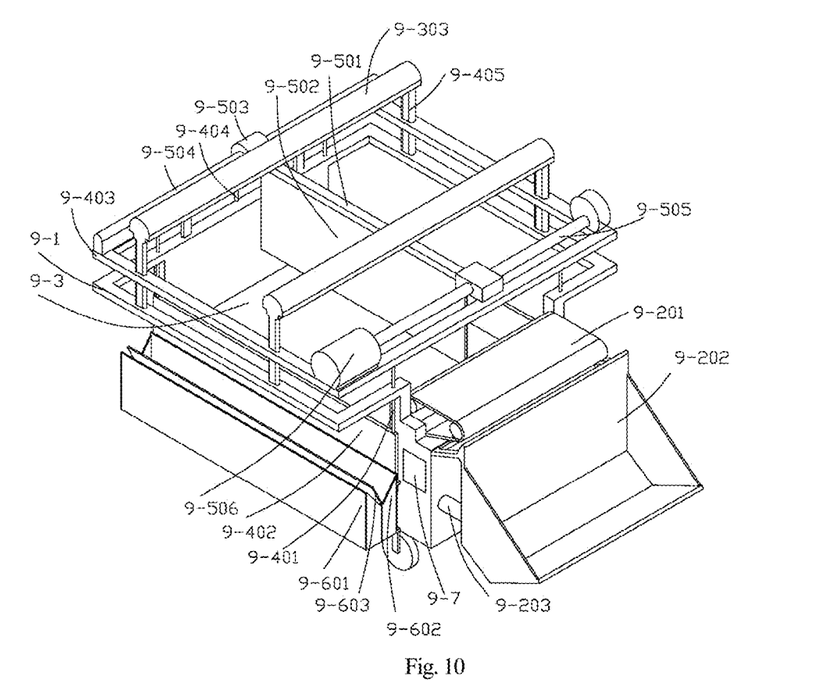
FIG. 10 is a 3D diagram of the fly maggot separator of the present invention.
Figure 11:
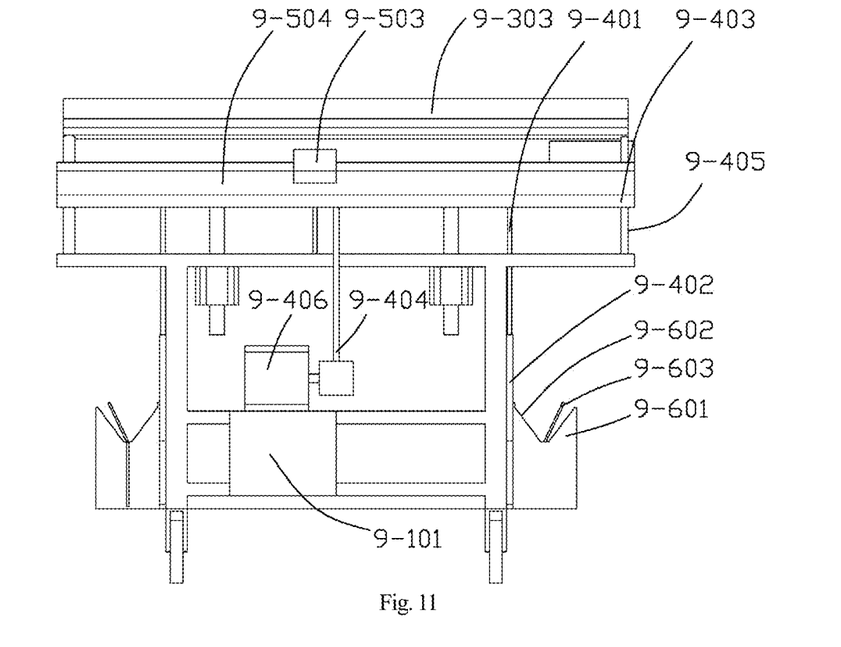
FIG. 11 is a rear view of the fly maggot separator of the present invention.
Figure 12:
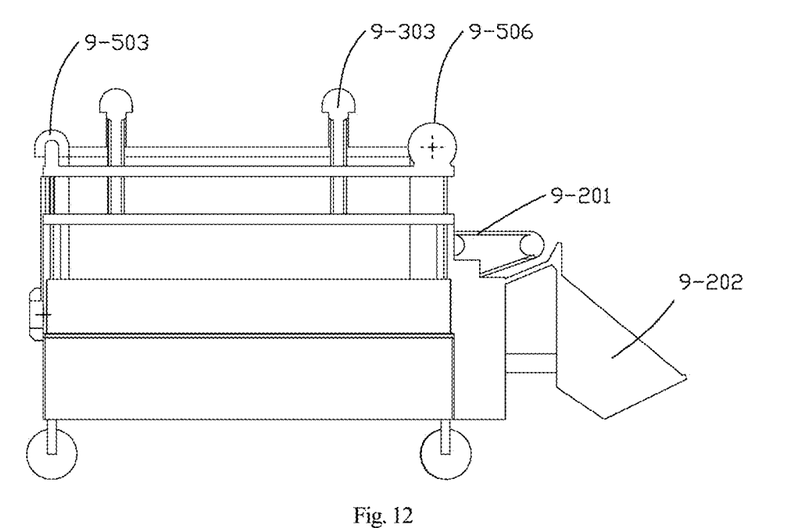
FIG. 12 is a lateral side view of the fly maggot separator of the present invention.
Figure 13:
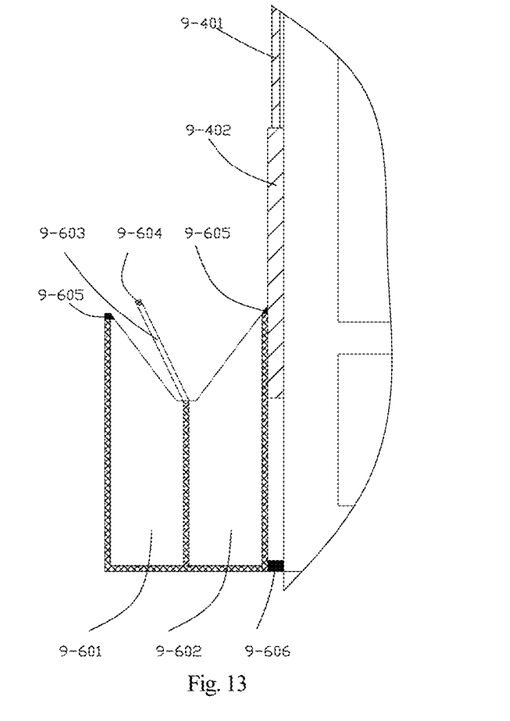
FIG. 13 is a structure diagram of the collecting unit of the fly maggot separator of the present invention.
Figure 14:
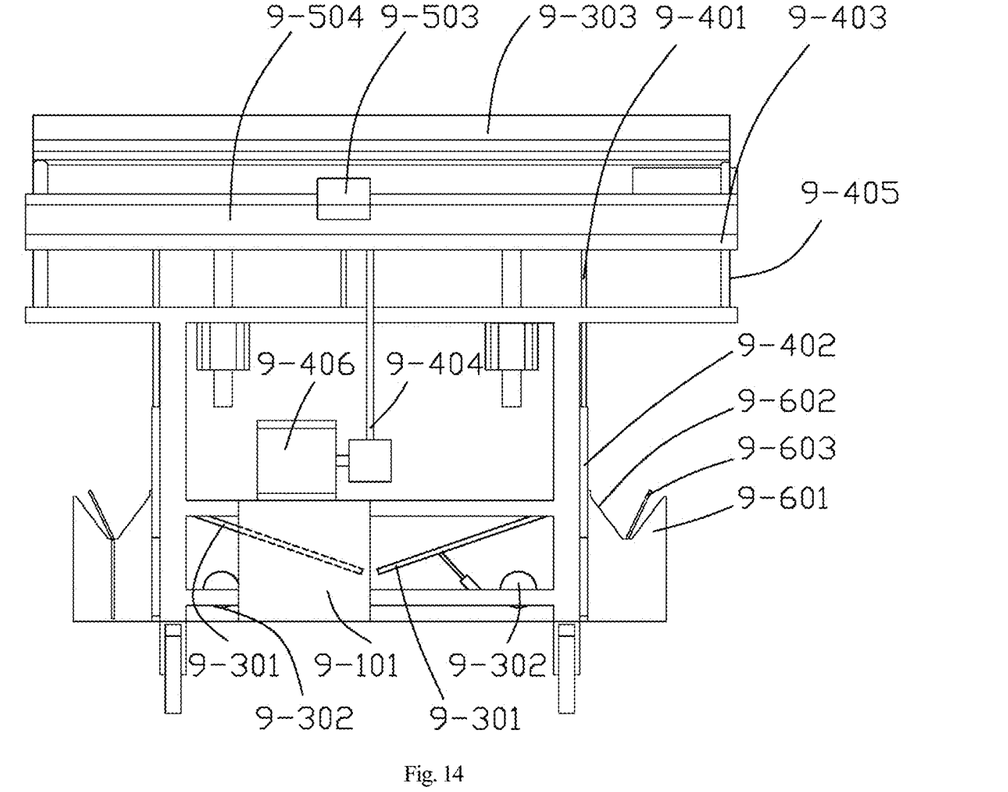
FIG. 14 is a diagram of baseplate on the bottom of the hopper and the motor of a fifth fly maggot separator of the present invention.
Figure 15:
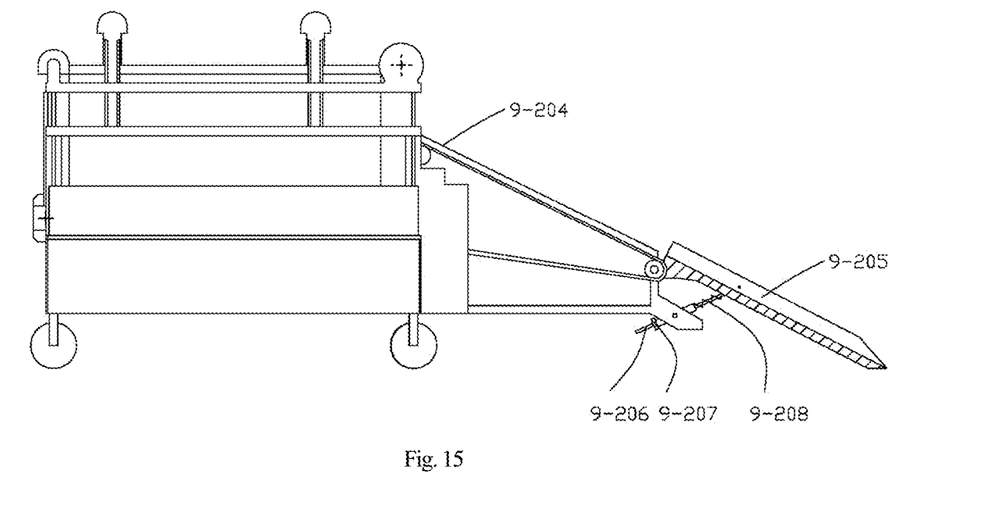
FIG. 15 is a schematic view of a second technical solution of the fly maggot separator feeding apparatus of the present invention.

Large-scale production can be realized in the culturing workshop. Once any anomaly of the temperature or humidity or any other fault signals are detected by the central control device 8, an alarm would be sounded to inform the workshop supervisors to handle in time to prevent the rapid pupation of fly maggots due to the excess culturing temperature. Additionally, the method of transferring the feeder 3 on to different rails by the transferring car adopted in the present invention realizes an integration of feeding process and the culturing bed and completes the feeding and culturing of the whole culture equipment process in a large-scale and high-efficiency way, thus overcoming the defects of the existing box-type culturing, cage-type culturing, frame-type culturing and pool-type culturing that are unable to realize high-efficiency and large-scale production or practical industrialized application due to the relatively low production efficiency, great labor intensity and tough working conditions.

Figure 4:
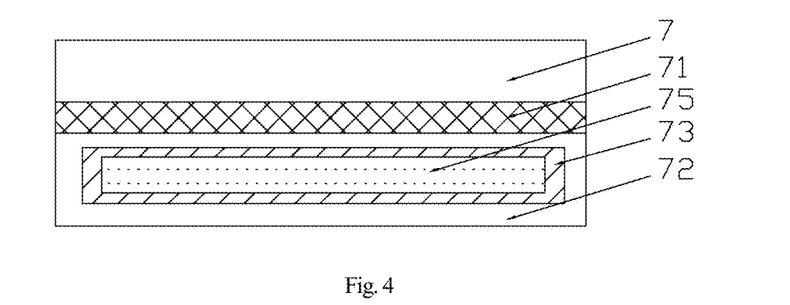
FIG. 4 is a structure diagram of culturing bed insulating layers of the present invention.

A temperature controllable insulating layer is arranged on the bottom of the culturing bed 7, consisting successively of a contact layer 71 and a thermally conductive layer 72. The heat-conducting medium 75 containing water or oil is arranged in thermally conductive layer, wherein the electromagnetic heating tubes 73 arranged and connected with the temperature controlling device of the culturing bed 74 through the electrical circuit. The temperature controlling device of the culturing bed 74 has electric connection with the central control device 8, the temperature sensor of the culturing bed evenly arranged at intervals in the contact layer 71 and medium temperature sensor arranged in thermal-conducting medium 75. With the setting of insulating layer, the temperature of the culture medium can be maintained within a range fittest for the growing of fly maggot, avoiding the influence of the temperature variation during the four different seasons and ensuring the large-scale and high-efficiency production all year round.

Figure 2:
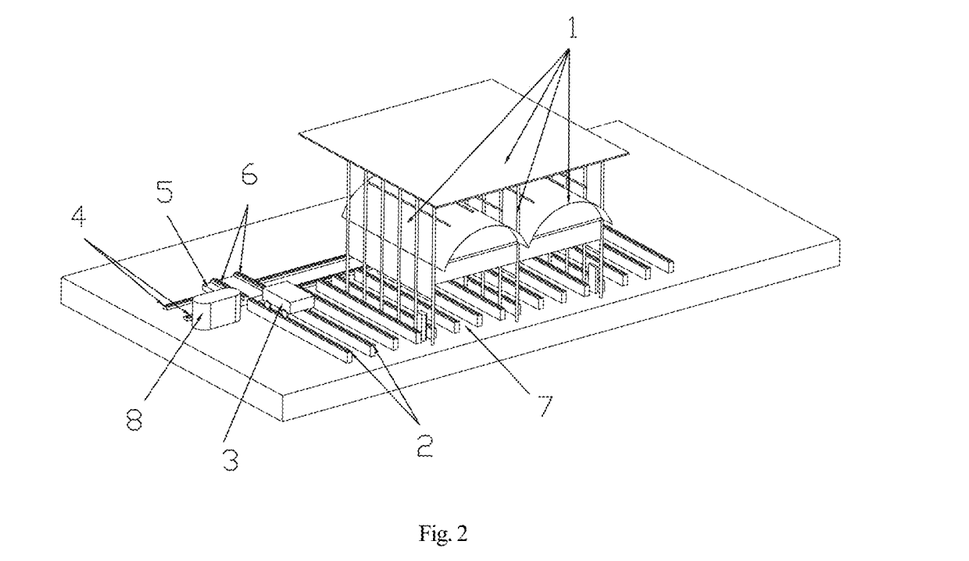
FIG. 2 is a structure diagram of culturing workshop and movable ceiling of the present invention.
Figure 3:
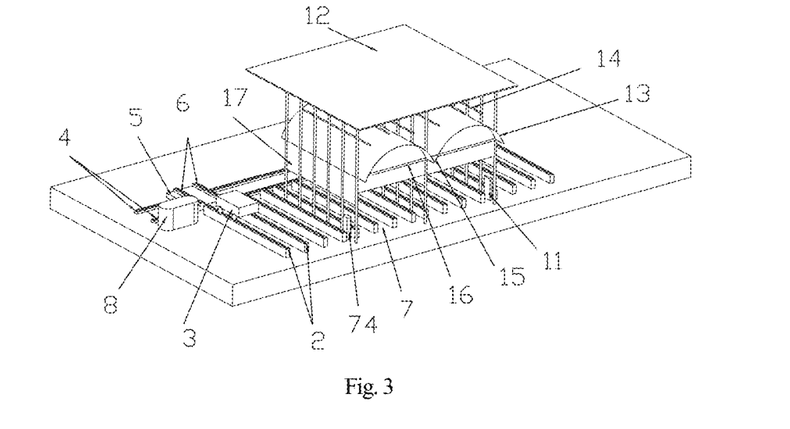
FIG. 3 is a locally detailed view of the FIG. 2.

The multi-functional ceiling 1 comprises a movable awning 12 opened and closed by the air temperature controlling device 11, which has electric connection with the central control device 8. A number of transparent plastic ceilings 13 are arranged below the movable awnings 12. The spouting water cooling pipes 14 are arranged between transparent plastic ceiling 13 and movable awnings 12. Between any two plastic ceilings 13 the water collecting troughs 15 are arranged for collecting rain and water sprayed from the spraying pipe. The setting of the air temperature controlling device 11 effectively keeps the humidity and temperature in the air under control, avoiding the temperature extremes. In the meantime, the temperature and humidity in the culturing workshop can be maintained within a range fittest for the growing of fly maggots.

The water collecting troughs 15 are connected on the bottom with the water curtain inlet pipes 16 arranged on the lower bottom of the plastic ceiling 13. The water curtain inlet pipes 16 are further provided with water pump thereon and are connected with the water curtain machines arranged on the sidewalls of the multi-functional ceiling. The air temperature controlling device 11 has electric connection with the water pump, the water curtain machines and the central control device 8 through the circuit. The water collecting trough 15 is used for collecting the cooling or humidifying water that can be recycled for the cooling water curtain, avoiding the waste of water resources and economizing the production cost.

Air temperature sensors and humidity sensors are arranged on top of and on the lower bottom of the plastic ceiling 13, wherein motorized roller shades 17 are arranged on the sidewalls. The air temperature controlling device 11 has electric connection with the air temperature sensor, humidity sensor and the motorized roller shades. The motorized roller shades are opened on time everyday for ventilation to prevent the deterioration of the fly maggots growing environment.

The central control device 8 is also connected with a data input device and a data output device. The data output device comprises the printers and the computers. The data input device may be digital touch screen type or the touch-tone type. A touch screen type is preferred in this embodiment. The data output device comprises printers and computers, which are used for collecting the dynamic data during the whole culturing process.

Embodiment 2

Please refer to FIG. 6 to FIG. 9. A feeder comprises the feeder rail car 3-2, whereon a movable platform 3-3 is provided capable of moving perpendicular to the direction of the feeder rail car 3-2 motion. Mounting holes are arranged on the movable platform 3-3, wherein a dismountable hopper 3-401 is plugged and connected with at least one distributing hopper 3-402 on the lower bottom.

The dismountable hopper is connected to a feed nozzle 3-403, wherein a feeding mechanism is coaxially arranged. According to different installation methods of the feed nozzles 3-403, the connecting and installing locations of the feeding mechanism and the rail car may differ too. For details, please refer to embodiment 2 and embodiment 3.

Please refer to FIG. 6 to FIG. 9. A feeder control apparatus 3-6 used for controlling the whole operation of the feeder rail car 3-2 is arranged on the feeder rail car 3-2 and is connected with and controlled by the central control device 8. The operation of fly maggot separator is also controlled by the central control device 8.

Please refer to FIG. 6 to FIG. 9. On the bottom of the feeder rail car 3-2, a first motor 3-7 is arranged for driving the rail car and has electric connection with the feeder control apparatus 3-6. The first motor 3-7 also comprises the continuously variable transmission. The traveling speed of the rail car can be accurately controlled by the feeder control apparatus 3-6 by way of a first motor 3-7 and the continuously variable transmission arranged thereon.

Please refer to FIG. 6 to FIG. 9. A manual signal input device and a wireless signal device having electric connection with the feeder control apparatus 3-6 are arranged on the feeder rail car 3-2. The manual signal input device comprises a digital LCD fixed on the outer side wall of the feeder rail car 3-2, and the wireless signal device comprises a wireless signal receiver 3-9 and a hand-held wireless signal transmitter fixed on the feeder rail car 3-2.

The wireless signal receiver 3-9 has electric connection with the feeder control apparatus 3-6. The feeding spacing of the feeder rail car, the traveling speed and distance of the movable platform can be controlled by utilizing the manual signal input device. By way of the wireless signal device, the feeder rail car can be remotely controlled with the wireless signal device to feed in different traveling speed and directions, which keeps the staff away from the bad environment of the production front line and makes labor-intensive work easier and simpler, greatly improving staffs production efficiency and working environment.

Please refer to FIG. 6 to FIG. 9. Two horizontal slides 3-301 connected with the feeder rail car 3-2 are arranged respectively on both ends of the bottom of the movable platform 3-3. The slide (3-301) and one side of the slide in the movable platform (3-3) is further arranged with a parallel ball screw. The slide is connected to and driven by a second motor 3-302, which has electric connection with the feeder control apparatus 3-6 through the circuit. After one feeding process of the feeder rail car 3-2, the parallel feeding screws are arranged in certain intervals to cover the ground between the feeding rails 3-2. During the next feeding process, the movable platform can be controlled and adjusted 3-3 to move for a certain distance, ensuring that the feed nozzle 3-403 is in middle of the feeding screws that has been fed during the previous process. Then the feeder rail car is controlled to feed again and the position of the feeding screw would be different from the last time.

Please refer to FIG. 6 to FIG. 9, the feeding mechanism comprises at least one screw conveyor 3-501 with one end plugged in the feed nozzle 3-403 and the other connected with the spindle of a third motor 3-502. The third motor 3-502 electrically connected with feeder control apparatus 3-6 is fixed on the feeder rail car 3-2

Please refer to FIG. 6 to FIG. 9. The feed nozzle 3-403 comprises a first feed nozzle, a second feed nozzle or a third feed nozzle. A gate 3-404 capable of opening and closing is arranged on a first feed nozzle and is connected with a push rod 3-405. The push rod is connected with a stepping motor 3-406, which is fixed on the feeder rail car 3-2 and has electric connection with the feeder control apparatus.

Embodiment 3

Please refer to FIG. 6 to FIG. 9. Except the feed nozzle and corresponding installation location of the feeding mechanism, other structures of the feeder are the same with the structures disclosed in the Embodiment 2. The third feed nozzle comprises a horizontal T-type hollow cylinder consisting of connecting cylinder 3-407 and a discharging cylinder 3-408. At least one discharging outlet 3-409 is arranged in the discharging cylinder 3-408 and a taintor valve is arranged thereon. A horizontal screw conveyor 3-411 is plugged in the connecting cylinder 3-407.

Embodiment 4

Please refer to FIG. 6 to FIG. 9. Except the feed nozzle and corresponding installation location of the feeding mechanism, other structures of the feeder are the same with the structures disclosed in the Embodiment 2. The second feed nozzle comprises a connector 3-412 and a 360° corrugated flexible hoses connected therewith. A screw conveyor is plugged in the connector 3-412. (not specified in the drawings)

Embodiment 5

Please refer to FIG. 10 to FIG. 15. A fly maggot separator comprises a vehicle body 9-1 of the fly maggot separator and a feeding apparatus arranged at the front end thereof. The feeding apparatus is connected with the front end of a groove-shaped hopper 9-3, which is fixed on the vehicle body 9-1 of the fly maggot separator and used for conveying fly maggots and compost residues. On the hopper 9-3 a vertical hoisting device is arranged, whereon a cleaning device capable of conducting reciprocating motion in a direction perpendicular to that of the vehicle body is disposed. Both ends of the hoisting device are connected with gates 9-402 in a hanging manner through connecting rods 9-401. The gates 9-402 are closely attached to the end faces of notches on both ends of the hopper. On the lateral lower part of the end faces, the collecting apparatuses are arranged respectively and fixed to the vehicle body.

Please refer to FIG. 10 to FIG. 15. The feeding apparatus comprises a first conveyor belt 9-201 driven by the motor of a first fly maggot separator. At the front end of a first conveyor belt a reversible first material shovel is further provided, with a telescopic push rod 9-203 arranged on the bottom. The feeding apparatus is used for continuously feeding the hopper 9-3 of the fly maggot separator during traveling process, therefore no manual feeding is needed and working efficiency is greatly improved. In the meantime, it has a broad application range and is applicable for different feeding processes.

Please refer to FIG. 10 to FIG. 15. The second technical scheme of feeding apparatus comprises a second conveyor belt 9-204, which is downward inclined to the ground with an angle less than or equal to 60°. On the front end of a second conveyor belt 9-204, a second material shovel 9-205 is pivotally mounted. In this technical scheme, a second material shovel 9-205 is almost attached to the ground on the front end when the fly maggot separator 9-1 moves forward. Then the culture medium is scooped up by the inclined second shovel 9-205 and then conveyed upper rearward through the inclined second conveyor belt 9-204 into the hopper-9-3. In the meantime a second material shovel 9-205 on the front end is provided with a pivoting design. When the culture medium feeding is not demanded, the nut 9-207 of the regulating rod 9-206 and the spring 9-208 at bottom of the material shovel 9-205 (the other end of the spring 9-208 is fixed to the vehicle body 9-1 of the fly maggot separator) can be screwed to hoist the material shovel 9-205 to an angle, thus increasing the distance between the front end of the material shovel and the ground until they are completely separated. When culture medium feeding is demanded, just performing the reverse operation is needed.

The advantage of this technical scheme is characterized by its simple structure and low cost.

Please refer to FIG. 10 to FIG. 15. The hoisting device comprises a support frame 9-403, which is connected on the bottom with a first worm 9-404 and a slide guiding rod 9-405 arranged in a vertical manner on the sidewall of the hopper 9-3. The first worm is connected with spindle of the vertically arranged motor 9-406 of a second fly maggot separator by way of the gear set. The hoisting device is used for adjusting the relative height of the cleaning plate of the cleaning device to the compost residue in the hopper, constantly reducing the height of the cleaning plate to scrape the compost residue layer by layer. By way of the automatic adjustment of the height of the hoisting device, the compost residue can be scraped layer by layer accurately, thus replacing the manual cleaning and free the staff from strenuous manual work. Please refer to FIG. 10 to FIG. 15. The cleaning device comprises a crossbar 9-501, which is connected in middle with the cleaning plate 9-502 in a hanging manner. A slide block 9-503, fixed on one end of the crossbar, is sheathed and sliding on the slide 9-503 arranged on top of the support frame 9-401. A second worm 9-505 is arranged on the other end of the crossbar 9-501 and is connected with the spindle of the motor 9-506 of a third fly maggot separator arranged on top of the support frame 9-401. Please refer to FIG. 10 to FIG. 15. The collecting apparatus comprises bevel residue collecting boxes 9-601 and bevel maggot collecting boxes. A pivoting first cover plate 9-603 that can be locked on both sides is further provided in the middle of the residue collecting box and the maggot collecting box. A torsional spring is arranged on the pivoted end of a first cover plate 9-603 and a lock portion 9-604 of the electromagnetic switch is arranged on the other end thereof. The lock portion 9-604 of the electromagnetic switch is matched to the electromagnetic locks respectively arranged on the residue collecting box and the vehicle body. The electromagnetic locks are also connected to the limit switch 9-606 sensing the height of the gates. Please refer to FIG. 10 to FIG. 15. A light source device 9-303 arranged in a hanging manner above the cleaning device is provided above the vehicle body 9-1 of the fly maggot separator. The both ends of bottom of the light source device are connected respectively with the slide guiding rod 9-405. The light source is infrared light or incandescent lamp. The slide guiding rod performs not only a guiding portion for the vertical hoisting of the hoisting device, but a support portion for the light source device.

Please refer to FIG. 10 to FIG. 15. A motor 9-101 of the fourth fly maggot separator used for driving is arranged on the bottom of the vehicle body 1.

Please refer to FIG. 10 to FIG. 15. On the vehicle body a control device is further provided and connected respectively with the motor of a first fly maggot separator, the motor 9-406 of a second fly maggot separator, the motor 9-506 of a third fly maggot separator, the motor 9-101 of the four fly maggot separator and the signal input device through the circuit. The signal input device comprises a touch screen of the fly maggot separator.

Working Principle

Please refer to FIG. 10 to FIG. 15. Owing to the only difference in the feeding methods between a first and a second feeding apparatus that may not affect the principle of fly maggots separating, this embodiment is explained by way of a first feeding apparatus in detail as follows, thus omitting the description of a second feeding apparatus. The present invention is used for mechanically separating the fly maggots from the compost residues after the conversion of the biomass waste for culture equipment and thus replacing the manual cleaning and separating process. The biological habit of fly maggots naturally pupating after maturation and the characteristics that the fly maggots need to pupate in a dark and dry environment are utilized by the present invention. The culture medium (or compost residues) after the growing period of the maggots (3 to 15 days) can be scooped up by a first material shovel 202 in the feeding apparatus on the front end of the fly maggot separator and then conveyed into the hopper 9-3 (approx. 10-40 cm depth) by a first conveyor belt 9-201. Then light source device 9-303 can be turned on and kept irradiating for a certain period, the fly maggots will move to the lower layer of the culture medium by natural habit (getting into the culture medium). Controlled by the preset parameter of the control device, the upper layer of the culture medium is scraped (swept) by the cleaning plate 9-502 of the cleaning device into the residue collecting box 9-601 on both sides of the fly maggot separator. At the moment, the maggot collecting box 9-602 is closely covered by a first cover plate 9-603. Through the height parameter preset by the control device, an automatic synchronized control of this process can be realized, that is, every time the fly maggots move in a certain distance to the lower part of the culture medium, the upper culture medium will be scraped (swept) into the collecting apparatus until the fly maggots are separated from the culture medium.

Once there are only fly maggots left in the hopper, the limit switch 9-606 is just actuated by the gate 9-402 and emits the electrical signal to the electromagnetic lock 9-602 arranged on the maggot collecting box. Then the electromagnetic switch of the electromagnetic lock is turned on and separated from the lock portion 9-604 (the steel-made lock portion attracted by electromagnetic lock through magnetic force generated by the current).

Through the torsional spring on pivoted end of a first cover plate 9-603, a first cover plate 9-603 is rotated to the other side to cover the residue collecting box 9-601 and then closely locked by another electromagnetic lock 9-605 with the same structure arranged thereon. At the same time when the limit switch 9-606 emits the electrical signal to the lock portion 9-604 arranged on the fly maggots box 9-602, an electrical signal is also emitted by the limit switch 9-604 to the control device, which after a certain pause controls the cleaning device to sweep all the fly maggots into the maggot collecting box 9-602 on both ends of the fly maggot separator.

Embodiment 6

Please refer to FIG. 10 to FIG. 15. By reference to the Embodiment 5, another kind of fly maggot separator is provided with all the parts of the fly maggot separator said in the embodiment 5. In the meantime, a baseplate 9-302 capable of opening and closing is arranged on the top of the hopper 9-3 and connected with the motor 9-302 of a fifth fly maggot separator by way of worm, worm wheel and the gear set. And the motor 9-302 of the firth fly maggot separator has electric connection with the control device. When the fly maggots are in large quantity, a method of discharging from the bottom is adopted to discharge the separated fly maggots from the bottom of the fly maggot separator.

Embodiment 7

The processing steps of the present invention are described in detail in this embodiment by reference to the accompanying drawings and the embodiment 1 to embodiment 6.

The present invention provides a culture equipment process with the utilization of said culture equipment, comprising the following steps:

1, Material preparation, preparing the biomass waste in the hopper and adding the auxiliary materials therein, then adjusting the water ratio of the biomass waste with the material mixer, which serves as the compost or culturing base.

2, preparation and incubation of the fly-blows.

3, adjustment and preparation of the culture equipment. Adjusting and controlling the temperature of contact layer 71 of the culturing bed 7 between 25-27° C. and adjusting the environment temperature below 37° C. The preferred temperature of the contact layer 71 is 32° C. and the preferred air temperature is 35° C. in this embodiment.

4, at first feeding of the day 1. The feeder as claimed in claim 1 is utilized to evenly and smoothly put a layer of culture medium as adjusted in step 1 on the culturing bed 7. The thickness of the culture medium should be 1-5 centimeter and the water ratio should be 45%-75%. Then scatter maggots as cultured in Step 2 into the culture medium, ensuring each gram of compost contains 2200-7000 fly maggots. The preferred quantity of the maggots is 5500 in this embodiment.

5, at second feeding of the day 1, adding culture medium of 45%-95% water ratio, 1-20 kg/m$^2$, ensuring the interval between a first and a second feeding within 4-16 hours.

6, on the day 2, continuing to add culture medium of 45%-95% water ratio and repeating step 3 and step 5, ensuring that the amount of culture medium within 1-20 kg/m$^2$, the interval and steps of feeding the same as requested in step 3 and step 5, and ventilation at 1-2 times a day.

7, on the day 3 to day n, continuing to add culture medium of 45%-95% water ratio and keeping the interval, steps, times and amount of culture medium adding and the ventilation frequency all the same as requested in step 5.

8, on the day n+1, stopping culture medium adding, separating fly maggots on several culturing beds from compost manually or by the fly maggot separator.

9, washing the fly maggots as separated in the step 8 in the washing machine and conveying them to the warm air dryer to obtain the dried maggots.

Preferably, the above-mentioned fly maggots are larvae of the housefly, *Musca sorbens, Lucilia cuprina, Cluysomya megacephala, Phaenicia cuprina, Calliphora erythrocephala, Muscina stabulans, sarcophaga peregrina* or soldier fly. The housefly is preferred in this embodiment.

Preferably, the biomass waste utilized in the Step 1 is the animal waste, kitchen waste or biomass processing waste. And the auxiliary materials are one or some combination of chicken or duck dung, extruded animal excrement, sawdust, rice chaff, spent mushroom compost, straw, tea residue and bran. The preferred biomass waste is the pig manure and the preferred auxiliary materials are sawdust and spent mushroom compost in this embodiment.

The foregoing disclosure of the invention with reference to the preferred embodiments is not intended to limit the present invention. Any of those skilled in this art can make possible changes or amendment without departing from the spirit and scope of the present invention. Thus the protection scope of the present invention is subject to the scope as defined in the claims.

The invention claimed is:

1. A fly maggot culture system comprising:
   a plurality of distributing rails, wherein each of the distributing rails comprises two rails parallel to each other and is configured to accommodate a culturing bed for fly maggots between the two rails;
   a pair of main rails perpendicular to the distributing rails;

a rail car configured to travel along the pair of main rails, wherein the rail car comprises transferring rails configured to respectively connect with the plurality of distributing rails as the rail car travels along the pair of main rails; and a feeder configured to travel along the transferring rails and along the plurality of distributing rails by the rail car.

2. The system of claim 1, further comprising a temperature regulator under the culturing bed and configured to regulate temperatures in the culturing bed.

3. The system of claim 1, further comprising a ceiling over the culturing bed;
wherein the ceiling comprises a movable awning controlled by an air temperature control device;
wherein the ceiling comprises transparent ceiling panels under the movable awning;
wherein the system further comprises spouting water cooling pipes between the transparent ceiling panels and the movable awning, and water collecting troughs between any two of the transparent ceiling panels and configured to collect rain water and water from the spouting water pipes.

4. The system of claim 1, wherein the feeder comprises a feeder cart;
wherein the feeder cart comprises a movable platform configured to move perpendicularly to a moving direction of the feeder cart;
wherein the feeder comprises a feeder control apparatus mounted on the feeder cart;
wherein the feeder comprises a dismountable hopper on the movable platform;
wherein the feeder comprises a sub-hopper connected to the dismountable hopper;
wherein the feeder comprises injection nozzles connected to the sub-hopper and a feeding mechanism arranged coaxially with the injection nozzles;
wherein the feeder comprises two horizontal slides connected with the rail car and respectively on both ends of the movable platform.

5. The system of claim 4, wherein the feeding mechanism comprises at least one screw conveyor.

6. The system of claim 4, wherein the injection nozzles comprises a first nozzle and a second nozzle;
wherein the first nozzle comprises a gate with a push rod connected thereto;
wherein the second nozzle comprises a rotatable hose connected thereto.

7. The system of claim 6, wherein the injection nozzles further comprises a third nozzle;
wherein the third nozzle comprises a horizontal "T" shaped hollow cylinder comprising a connecting cylinder and a discharging cylinder joined together;
wherein the connecting cylinder comprises a screw conveyor therein; and
wherein the discharging cylinder comprises at least three discharging outlets thereon and Tainter valves at the discharging outlets.

8. The system of claim 1, further comprising a fly maggot separator and a hopper;
wherein the fly maggot separator is configured to separate fly maggots in the culturing bed from compost residue in the culturing bed;
wherein the hopper is configured to transport the fly maggots and the compost residue.

9. The system of claim 8, wherein the fly maggot separator comprises a feeding apparatus configured to move the compost residue into the hopper.

10. The system of claim 8, wherein the hopper comprises a bottom door.

11. A method of using the system of claim 1, comprising:
spreading a layer of culture medium into the culturing bed by using the feeder;
introducing fly maggots into the layer of culture medium, wherein the fly maggots are selected from the group consisting of housefly maggots, *Musca sorbens* maggots, *Lucilia cuprina* maggots, *Chrysomya megacephala* maggots, *Phaenicia cuprina* maggots, *Calliphora erythrocephala* maggots, *Muscina stabulans* maggots, *sarcophaga peregrinaperegrine* maggots, soldier fly maggots, and any combinations thereof;
replenishing the culture medium into the culturing bed;
harvesting the fly maggots from the culturing bed; and
washing and drying the fly maggots.

12. The method of claim 11, wherein the layer of culture medium has a thickness of 1 to 5 cm and a water ratio of 45%-75%.

* * * * *